US008920514B2

(12) United States Patent
Gregory et al.

(10) Patent No.: US 8,920,514 B2
(45) Date of Patent: Dec. 30, 2014

(54) SYSTEMS AND METHODS FOR INTRODUCING AND APPLYING A BANDAGE STRUCTURE WITHIN A BODY LUMEN OR HOLLOW BODY ORGAN

(75) Inventors: Kenton W. Gregory, Portland, OR (US); Amanda Dayton, Portland, OR (US)

(73) Assignee: Providence Health System—Oregon, Portland, OR (US)

( * ) Notice: Subject to any disclaimer, the term of this patent is extended or adjusted under 35 U.S.C. 154(b) by 318 days.

(21) Appl. No.: 12/004,297

(22) Filed: Dec. 20, 2007

(65) Prior Publication Data
US 2008/0287907 A1   Nov. 20, 2008

Related U.S. Application Data

(63) Continuation of application No. 11/805,543, filed on May 23, 2007, now abandoned.

(60) Provisional application No. 60/802,654, filed on May 23, 2006.

(51) Int. Cl.
| | | |
|---|---|---|
| A61F 2/02 | (2006.01) | |
| A61F 2/04 | (2013.01) | |
| A61F 2/06 | (2013.01) | |
| A61F 2/958 | (2013.01) | |
| A61L 15/28 | (2006.01) | |
| A61F 2/962 | (2013.01) | |

(52) U.S. Cl.
CPC . *A61F 2/04* (2013.01); *A61F 2/958* (2013.01); *A61L 15/28* (2013.01); *A61F 2/962* (2013.01)
USPC ............. 623/23.72; 623/1.11; 623/23.65

(58) Field of Classification Search
USPC ......... 606/191, 192, 194, 198, 108; 623/1.11, 623/23.64, 1.47, 1.21, 1.22, 23.7, 2.11, 623/1.23, 23.65, 1.12; 602/57, 48–52; 604/103.07, 103.05, 508, 509, 514, 604/96.01, 163, 171
See application file for complete search history.

(56) References Cited

U.S. PATENT DOCUMENTS

| | | |
|---|---|---|
| 2,610,625 A | 9/1952 | Sifferd et al. |
| 2,858,830 A | 11/1958 | Robins |

(Continued)

FOREIGN PATENT DOCUMENTS

| | | |
|---|---|---|
| EP | 0353972 | 2/1990 |
| EP | 0477979 | 9/1991 |

(Continued)

OTHER PUBLICATIONS

Park et al., "Platelet derived growth factor releasing chitosan sponge for periodontal bone regeneration." Biomaterials, vol. 21: 153-159, 2000.

(Continued)

*Primary Examiner* — Gregory Anderson
*Assistant Examiner* — Christopher L Templeton
(74) *Attorney, Agent, or Firm* — Miller Nash LLP; Chandra E. Eidt

(57) ABSTRACT

Systems and methods provide intraluminal delivery of a bandage structure within a body lumen or hollow body organ, e.g., for treating an injured gastrointestinal tract or an esophageal hemorrhage in a non-invasive way using endoscopic visualization. The systems and methods can be sized and configured to apply a chitosan bandage structure within a body lumen or hollow body organ, to take advantage of the mucoadhesive, antimicrobial, hemostatic, and potential accelerated wound healing properties of the chitosan material.

16 Claims, 7 Drawing Sheets

(56) References Cited

U.S. PATENT DOCUMENTS

| | | | | |
|---|---|---|---|---|
| 2,923,664 A | | 2/1960 | Cook et al. | |
| 3,551,556 A | | 12/1970 | Kilment et ai. | |
| 3,632,754 A | | 1/1972 | Balassa | |
| 3,800,792 A | | 4/1974 | McKnight et al. | |
| 3,801,675 A | | 4/1974 | Russell | |
| 3,849,238 A | | 11/1974 | Gould et al. | |
| 3,902,497 A | | 9/1975 | Casey | |
| 3,911,116 A | | 10/1975 | Balassa | |
| 3,954,493 A | | 5/1976 | Battista et al. | |
| 3,977,406 A | | 8/1976 | Roth | |
| 4,040,884 A | | 8/1977 | Roth | |
| 4,056,103 A | | 11/1977 | Kaczmarzyk et al. | |
| 4,068,757 A | | 1/1978 | Casey | |
| 4,094,743 A | | 6/1978 | Leuba | |
| 4,195,175 A | | 3/1980 | Peniston et al. | |
| 4,292,972 A | | 10/1981 | Palwelchak et al. | |
| 4,373,519 A | | 2/1983 | Errede et al. | |
| 4,394,373 A | | 7/1983 | Malette et al. | |
| 4,452,785 A | | 6/1984 | Malette et al. | |
| 4,460,642 A | | 7/1984 | Errede et al. | |
| 4,501,835 A | | 2/1985 | Berke | |
| 4,524,064 A | | 6/1985 | Nambu | |
| 4,532,134 A | | 7/1985 | Malette et al. | |
| 4,533,326 A | | 8/1985 | Anthony | |
| 4,541,426 A | | 9/1985 | Webster | |
| 4,599,209 A | | 7/1986 | Dautzenberg et al. | |
| 4,651,725 A | | 3/1987 | Kifune et al. | |
| 4,684,370 A | | 8/1987 | Barrett | |
| 4,699,135 A | | 10/1987 | Motosugi et al. | |
| 4,759,348 A | | 7/1988 | Cawood | |
| 4,772,275 A | * | 9/1988 | Erlich | 604/523 |
| 4,772,419 A | | 9/1988 | Malson et al. | |
| 4,833,237 A | | 5/1989 | Kawamura et al. | |
| 4,877,030 A | * | 10/1989 | Beck et al. | 606/195 |
| 4,948,540 A | | 8/1990 | Nigam | |
| 4,952,618 A | | 8/1990 | Olsen | |
| 4,956,350 A | | 9/1990 | Mosbey | |
| 4,958,011 A | | 9/1990 | Bade | |
| 4,960,413 A | | 10/1990 | Sagar et al. | |
| 4,973,493 A | | 11/1990 | Guire | |
| 4,977,892 A | | 12/1990 | Ewall | |
| 5,006,071 A | | 4/1991 | Carter | |
| 5,007,926 A | * | 4/1991 | Derbyshire | 623/1.15 |
| 5,024,841 A | | 6/1991 | Chu et al. | |
| 5,035,893 A | | 7/1991 | Shioya et al. | |
| 5,062,418 A | | 11/1991 | Dyer et al. | |
| 5,110,604 A | | 5/1992 | Chu et al. | |
| 5,116,824 A | | 5/1992 | Miyata et al. | |
| 5,147,387 A | * | 9/1992 | Jansen et al. | 606/108 |
| 5,154,928 A | | 10/1992 | Andrews | |
| 5,192,307 A | * | 3/1993 | Wall | 623/1.2 |
| 5,206,028 A | | 4/1993 | Li | |
| 5,254,301 A | | 10/1993 | Sessions et al. | |
| 5,300,494 A | | 4/1994 | Brode, II et al. | |
| 5,376,376 A | * | 12/1994 | Li | 424/443 |
| 5,378,472 A | | 1/1995 | Muzzarelli | |
| 5,411,549 A | * | 5/1995 | Peters | 623/1.15 |
| 5,420,197 A | | 5/1995 | Lorenz et al. | |
| 5,441,515 A | * | 8/1995 | Khosravi et al. | 606/194 |
| 5,443,500 A | * | 8/1995 | Sigwart | 623/1.17 |
| 5,449,382 A | * | 9/1995 | Dayton | 623/1.15 |
| 5,454,719 A | | 10/1995 | Hamblen | |
| 5,525,710 A | | 6/1996 | Unger et al. | |
| 5,527,337 A | * | 6/1996 | Stack et al. | 606/198 |
| 5,571,181 A | | 11/1996 | Li | |
| 5,578,075 A | * | 11/1996 | Dayton | 623/1.15 |
| 5,593,434 A | * | 1/1997 | Williams | 128/898 |
| 5,597,581 A | | 1/1997 | Kaessmann et al. | |
| 5,618,299 A | * | 4/1997 | Khosravi et al. | 623/1.2 |
| 5,643,596 A | | 7/1997 | Pruss et al. | |
| 5,647,857 A | * | 7/1997 | Anderson et al. | 604/264 |
| 5,649,977 A | * | 7/1997 | Campbell | 623/1.15 |
| 5,700,476 A | | 12/1997 | Rosenthal et al. | |
| 5,738,860 A | | 4/1998 | Schonfeldt | |
| 5,756,111 A | | 5/1998 | Yoshikawa et al. | |
| 5,765,682 A | * | 6/1998 | Bley et al. | 206/363 |
| 5,797,960 A | | 8/1998 | Stevens et al. | |
| 5,821,271 A | | 10/1998 | Roenigk | |
| 5,827,265 A | * | 10/1998 | Glinsky et al. | 606/8 |
| 5,836,970 A | | 11/1998 | Pandit | |
| 5,840,777 A | | 11/1998 | Eagles et al. | |
| 5,858,292 A | | 1/1999 | Dragoo et al. | |
| 5,858,350 A | | 1/1999 | Vournakis et al. | |
| 5,952,618 A | | 9/1999 | Deslauriers | |
| 5,957,929 A | * | 9/1999 | Brenneman | 623/1.11 |
| 5,961,478 A | | 10/1999 | Timmermans | |
| 5,984,963 A | * | 11/1999 | Ryan et al. | 623/1.11 |
| 6,042,877 A | | 3/2000 | Lyon et al. | |
| 6,048,360 A | * | 4/2000 | Khosravi et al. | 623/1.11 |
| 6,054,122 A | | 4/2000 | MacPhee et al. | |
| 6,103,369 A | | 8/2000 | Lucast et al. | |
| 6,124,273 A | | 9/2000 | Drohan et al. | |
| 6,156,330 A | | 12/2000 | Tsukada et al. | |
| 6,162,241 A | | 12/2000 | Coury et al. | |
| 6,200,325 B1 | * | 3/2001 | Durcan et al. | 606/108 |
| 6,225,521 B1 | | 5/2001 | Gueret | |
| 6,238,431 B1 | * | 5/2001 | Asimacopoulos | 623/1.15 |
| 6,270,515 B1 | * | 8/2001 | Linden et al. | 606/213 |
| 6,406,712 B1 | | 6/2002 | Rolf | |
| 6,448,462 B2 | | 9/2002 | Groitzsch et al. | |
| 6,454,787 B1 | | 9/2002 | Maddalo et al. | |
| 6,485,667 B1 | | 11/2002 | Tan | |
| 6,486,285 B2 | | 11/2002 | Fujita | |
| 6,548,081 B2 | | 4/2003 | Sadozai et al. | |
| 6,548,569 B1 | | 4/2003 | Williams et al. | |
| 6,552,244 B1 | | 4/2003 | Jacques et al. | |
| 6,565,878 B2 | | 5/2003 | Schoenfedlt et al. | |
| 6,566,577 B1 | | 5/2003 | Addison et al. | |
| 6,599,891 B2 | | 7/2003 | North et al. | |
| 6,693,180 B2 | | 2/2004 | Lee et al. | |
| 6,726,712 B1 | * | 4/2004 | Raeder-Devens et al. | 623/1.11 |
| 6,749,601 B2 | * | 6/2004 | Chin | 606/1 |
| 6,750,262 B1 | | 6/2004 | Hahnle et al. | |
| 6,764,504 B2 | * | 7/2004 | Wang et al. | 623/1.11 |
| 6,827,731 B2 | * | 12/2004 | Armstrong et al. | 623/1.12 |
| 6,855,860 B2 | | 2/2005 | Ruszczak et al. | |
| 6,863,924 B2 | | 3/2005 | Ranganathan et al. | |
| 6,864,245 B2 | | 3/2005 | Vournakis et al. | |
| 6,992,233 B2 | | 1/2006 | Drake et al. | |
| 7,019,191 B2 | | 3/2006 | Looney et al. | |
| 7,115,141 B2 | * | 10/2006 | Menz et al. | 623/1.12 |
| 7,371,403 B2 | | 5/2008 | McCarthy et al. | |
| 7,482,503 B2 | | 1/2009 | Gregory et al. | |
| 7,485,138 B2 | * | 2/2009 | Fearnot et al. | 623/1.1 |
| 7,491,227 B2 | * | 2/2009 | Yang | 623/1.15 |
| 7,546,812 B2 | | 6/2009 | Eastin et al. | |
| 7,671,102 B2 | | 3/2010 | Gaserod et al. | |
| 7,763,065 B2 | * | 7/2010 | Schmid et al. | 623/1.15 |
| 7,820,872 B2 | | 10/2010 | Gregory et al. | |
| 7,850,709 B2 | | 12/2010 | Cummins et al. | |
| 7,897,832 B2 | | 3/2011 | McAdams et al. | |
| 8,043,359 B2 | * | 10/2011 | Edin | 623/1.15 |
| 8,063,265 B2 | | 11/2011 | Beck et al. | |
| 2001/0045177 A1 | | 11/2001 | Harvey et al. | |
| 2002/0035391 A1 | | 3/2002 | Mikus et al. | |
| 2002/0161376 A1 | * | 10/2002 | Barry et al. | 606/108 |
| 2004/0193243 A1 | * | 9/2004 | Mangiardi et al. | 623/1.11 |
| 2005/0036955 A1 | | 2/2005 | DeGould | |
| 2005/0123581 A1 | | 6/2005 | Ringeisen et al. | |
| 2005/0137512 A1 | | 6/2005 | Campbell et al. | |
| 2005/0143817 A1 | | 6/2005 | Hunter et al. | |
| 2005/0147656 A1 | | 7/2005 | McCarthy et al. | |
| 2005/0240137 A1 | | 10/2005 | Zhu et al. | |
| 2006/0004314 A1 | | 1/2006 | McCarthy et al. | |
| 2006/0008419 A1 | | 1/2006 | Hissink et al. | |
| 2006/0079957 A1 | | 4/2006 | Chin et al. | |
| 2006/0083710 A1 | | 4/2006 | Joerger et al. | |
| 2006/0089702 A1 | * | 4/2006 | Cervantes | 623/1.11 |
| 2006/0184224 A1 | * | 8/2006 | Angel | 623/1.11 |
| 2006/0211973 A1 | * | 9/2006 | Gregory et al. | 602/49 |
| 2007/0021703 A1 | | 1/2007 | McCarthy et al. | |
| 2007/0066920 A1 | | 3/2007 | Hopman et al. | |
| 2007/0083137 A1 | | 4/2007 | Hopman et al. | |
| 2007/0237811 A1 | | 10/2007 | Scherr | |

(56) References Cited

U.S. PATENT DOCUMENTS

| | | | |
|---|---|---|---|
| 2007/0255194 A1 | 11/2007 | Gudnason et al. | |
| 2007/0255243 A1 | 11/2007 | Kaun et al. | |
| 2007/0276308 A1 | 11/2007 | Huey et al. | |
| 2008/0132990 A1* | 6/2008 | Richardson | 623/1.12 |
| 2008/0241229 A1 | 10/2008 | Li et al. | |

FOREIGN PATENT DOCUMENTS

| | | | |
|---|---|---|---|
| EP | 0643963 | 3/1995 | |
| EP | 1462123 | 9/2004 | |
| JP | 60-142927 | 7/1985 | |
| JP | 62-039506 | 2/1987 | |
| JP | 63-090507 | 4/1988 | |
| JP | 07-116241 | 5/1995 | |
| JP | 11-342153 | 12/1999 | |
| JP | 2002-233542 | 8/2002 | |
| WO | WO 95/05794 | 3/1995 | |
| WO | WO 98/48861 | 11/1998 | |
| WO | WO 99/02587 | 1/1999 | |
| WO | WO 00/56256 | 9/2000 | |
| WO | WO 02102276 | * 12/2002 | A61F 15/00 |
| WO | WO 03/047643 | 6/2003 | |
| WO | WO 03/079946 | 10/2003 | |
| WO | WO 03/092756 | 11/2003 | |
| WO | WO 03/101310 | 12/2003 | |
| WO | WO 2004/047695 | 6/2004 | |
| WO | WO 2004/060412 | 7/2004 | |
| WO | WO 2005062880 | 7/2005 | |
| WO | WO 2006049463 | 5/2006 | |
| WO | WO 2006071649 | 7/2006 | |
| WO | WO 2007009050 | 1/2007 | |
| WO | WO 2007056066 | 5/2007 | |
| WO | WO 2007074327 | 7/2007 | |
| WO | WO 2008033462 | 3/2008 | |
| WO | WO 2008036225 | 3/2008 | |

OTHER PUBLICATIONS

Allan et al., "Biomedical Applications of Chitin and Chitosan." Chitin, Chitosan, and Related Enzymes—Accademic Press, Inc.: 119-133, 1984.
Anema et al., "Potential Uses of Absorbable Fibrin Adhesive Bandage for Genitourinary Trauma." World Journal of Surgery, vol. 25: 1573-1577, 2001.
Bégin et al., "Antimicrobial films produced from chitosan." International Journal of Biological Macromolecules, vol. 26: 63-67, 1999.
Chan et al., "Comparision of Poly-N-acetyl Glucosamine (P-GlcNAc) with Absorbable Collagen (Actifoam), and Fibrin Sealant (Bolheal) for Achieving Hemostasis in a Swine Model of Splenic Hemorrhage." The Journal of Trauma: 454-458, 2000.
Cole et al., "A pilot study evaluating the efficacy of a fully acetylated poly-N-acetyl glucosamine membrane formulation as a topical hemostatic agent." Surgery, vol. 126, No. 3: 510-517, 1999.
Kiley, Kevin, "Department of the Army memo." Jul. 20, 2005.
Kumar, Ravi, "Chitin and chitosan fibres: A review." Bulletin of Material Science: vol. 22, No. 5: 905-915, Aug. 1999.
Luo et al., "The role of poly(ethylene glycol) in the formation of silver nanoparticles." Journal of Colloid and Interface Science, vol. 288: 444-448, 2005.
Malette et al., "Chitosan: A New Hemostatic." The Annals of Thoratic Surgery, vol. 36, No. 1: 55-58, Jul. 1983.
Martin et al., "Medical applications of poly-4-hydroxybutyrate: a strong flexible absorbable biomaterial." Biochemical Engineering Journal, vol. 16: 97-105, 2003.
Mi et al., "Fabrication and characterization of a sponge-like asymmetric chitosan membrane as a wound dressing." Biomaterials, vol. 22: 165-173, 2001.
Moody, Robin J., "HemCon bandage stakes claim to soldier's kit bag." Portland Business Journal, Nov. 4, 2005.
Ohshima et al., "Clinical Application of Chitin Non-Woven Fabric as Wound Dressing." European Journal of Plastic Surgery, vol. 10: 66-69, 1987.
Ohshima et al., "Clinicai application of new chitin non-woven fabric and new chitin sponge sheet as wound dressing." European Journal of Plastic Surgery, vol. 14: 207-211, 1991.
Olsen et al., "Bomedical Applicatons of Chitin and its Derivatives." Chitin and Chitosan: Poceedings from the 4th International Conference on Chitin and Chitosan, 813-829, 1988.
Percot et al., "Optimization of Chitin Extraction from Shrimp Shells." Biomacromolecules, vol. 4: 12-18, 2003.
Pusateri et al., "Advanced Hemostatic Dressing Development Program: Animal Model Selection Criteria and Results of a Study of Nine Hemostatic Dressings in a Model of Severe Large Venous Hemorrhage and Hepatic Injury in Swine." The Journal of Trauma, vol. 55: 518-526, 2003.
Sandford, Paul A., "Chitosan: Commercial Uses and Potential Applications." Chitin and Chitosan: Proceedings from the 4th International Conference on Chitin and Chitosan, 51-69, 1988.
Sandford et al., "Biomedical Applications of High-Purity Chitosan." Water-Soluble Polymers: Chapter 28: 430-445, 1991.
Sandford, Paul A., "Biomedical Applications of New Forms of Chitin/Chitosan." Chitin Derivatives in Life Science, 12pp., 1992.
Sondeen et al., "Comparison of 10 Different Hemostatic Dressings in an Aortic Injury." The Journal of Trauma, vol. 54, No. 2: 280-285, 2003.
Wedmore et al., "A Special Report on the Chitosan-based Hemostatic Dressing: Experience in Current Combat Operations." The Journal of Trauma, vol. 60: 655-658, 2006.
Wilson, J.R., "The Army's Greatest Inventions." U.S. Army Materiel Command, pp. 30-37, 2005.
Bendix., "Chemical synthesis of polyactide and its copolymers for medical applications." Polymer Degradation and Stability, vol. 59: 129-135, 1998.
Schoof et al., "Control of Pore Structure and Size in Freeze-Dried Collagen Sponges." Journal of Biomedical Material Research, vol. 58: 352-357, 2001.
Wu et al., "Development of In Vitro Adhesion Test for Chitosan Bandages." Society for Biomaterials 30th Annual Meeting Transactions, 2005, 1pg.
Database WPI, Week 200873 Thomson Scientific, London GB, AN 2008-M34232, XP002695569 & CN 101138648, Mar. 12, 2008.

* cited by examiner

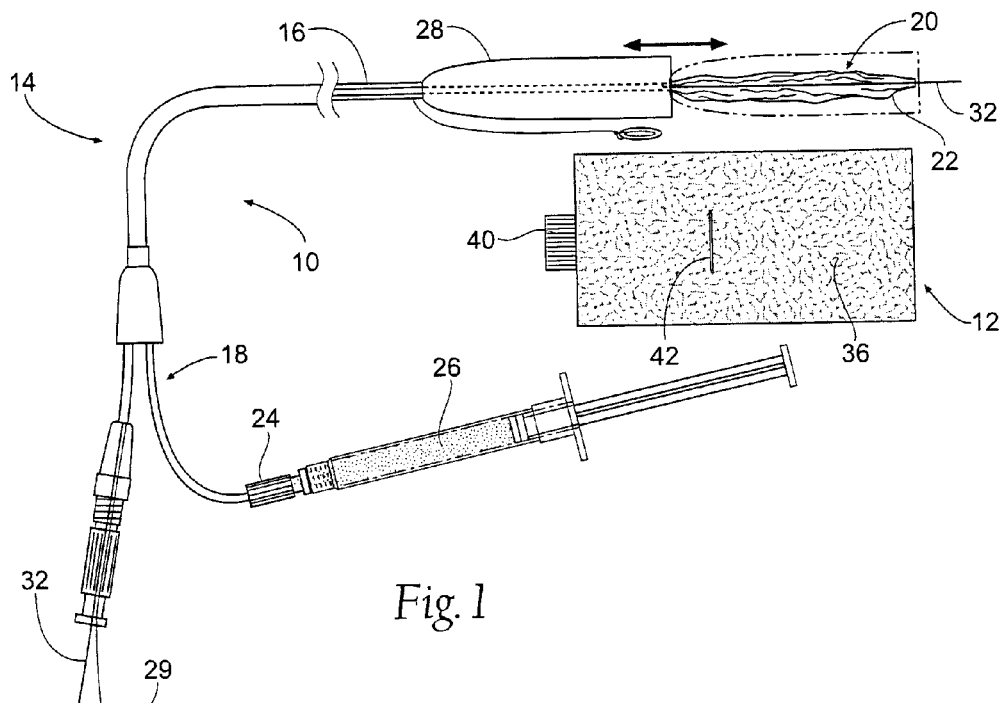
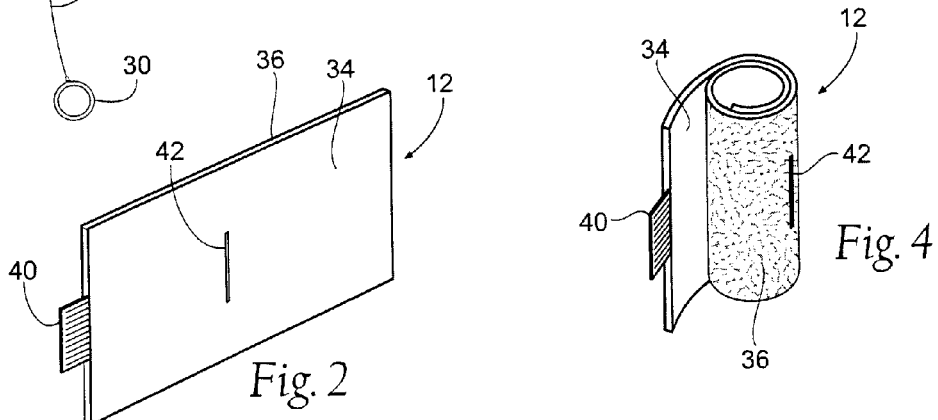
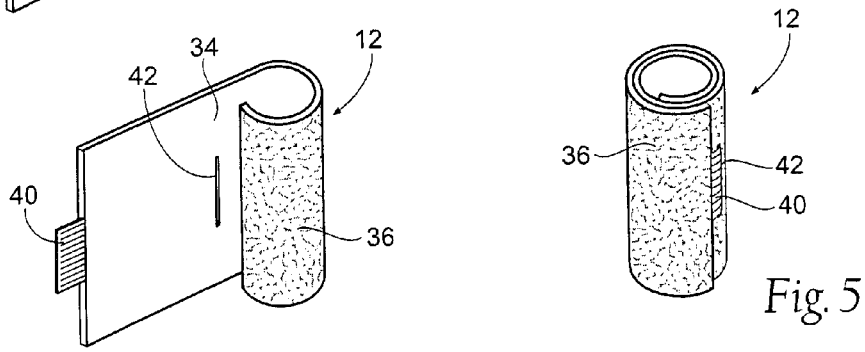

SYSTEMS AND METHODS FOR INTRODUCING AND APPLYING A BANDAGE STRUCTURE WITHIN A BODY LUMEN OR HOLLOW BODY ORGAN

RELATED APPLICATIONS

This application is a continuation of patent application Ser. No. 11/805,543 filed 23 May 2007, now abandoned, which claims the benefit of provisional patent application Ser. No. 60/802,654filed 23 May 2006.

This application is related to U.S. patent application Ser. No. 11/084,688, filed on Mar. 17, 2005, entitled "Systems and Methods for Hemmorrhage Control and/or Tissue Repair."

FIELD OF THE INVENTION

The invention is generally directed to systems and methods to introduce and deploy tissue bandage structures within a body lumen or hollow body organ, such, e.g., as within the gastrointestinal tract.

BACKGROUND OF THE INVENTION

Currently, there exists no overwhelmingly accepted treatment for gastrointestinal, specifically esophageal bleeding with etiology such as; esophageal ulcers, esophagitis, Mallory Weis tears, Booerhave's syndrome, esophageal varices, anastomosis, fistula, and endoscopic procedures.

Electro-cautery and sclerotherapy are two existing treatments for esophageal hemorrhage, however both run a risk of perforation to the esophagus. Electro-cautery requires a large amount of pressure to be applied to the wall of the esophagus and also inherently damages tissue. Sclerotherapy consists of injecting a hardening agent in to the area of the injury with a needle. Clipping is another method of treatment; it consists of a two or three-pronged clip that can be inserted into the mucosa of the esophagus to constrict the area of the bleeding. If applied correctly, clipping is effective in controlling hemorrhage, however clips are difficult to deploy. Often, the clip is not inserted deep enough into the mucosa and sloughs off before the desired time.

SUMMARY OF THE INVENTION

The invention provides systems and methods for applying a bandage structure within a body lumen or a hollow body organ, e.g., for treating an injured gastrointestinal tract or an esophageal hemorrhage.

Another aspect of the invention includes systems and methods for placing a bandage structure within a body lumen or hollow body organ in a non-invasive way using endoscopic visualization.

The systems and methods do not involve the use of any sharp edges or points. The systems and methods do not involve the use of a point pressure, as existing treatment options require. Only moderate circumferential pressure is required to apply the bandage structure. The systems and methods adapt well to tools and techniques usable by gastroenterologists.

The systems and methods can be sized and configured to apply a chitosan bandage structure within a body lumen or hollow body organ, to take advantage of the mucoadhesive, antimicrobial, hemostatic, and potential accelerated wound healing properties of the chitosan material. Drug delivery and cell therapy with a chitosan bandage structure as a delivery matrix are also made possible.

Other features and advantages of the invention shall be apparent based upon the accompanying description, drawings, and claims.

BRIEF DESCRIPTION OF THE DRAWINGS

FIG. 1 is a plane view of an intraluminal delivery system for introducing and applying a bandage structure within a body lumen or hollow body organ.

FIG. 2 is perspective view of the bandage structure that is sized and configured for deployment by the system shown in FIG. 1.

FIGS. 3 to 5 show the rolling of the bandage structure into a low profile condition prior to deployment by the system shown in FIG. 1.

DESCRIPTION OF THE PREFERRED EMBODIMENT

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. The Intraluminal Delivery System

FIG. 1 shows an intraluminal delivery system 10 for introducing and applying a bandage structure 12 within a body lumen or hollow body organ. The delivery system 10 includes a bandage structure 12 and a delivery device 14 that is sized and configured to deliver and deploy the bandage structure 12 at a targeted tissue region within a body lumen or hollow body organ. The delivery device 14 is sized and configured to deploy the bandage structure 12 while preventing it from contacting tissue lining the body lumen or hollow body organ until the desired time of deployment. The delivery device 14 not only provides a barrier between the bandage structure 12 and tissue within the body lumen or hollow body organ during introduction, but also provides a means to deploy the bandage structure 12 into contact with the tissue at the desired time.

Figure 10:
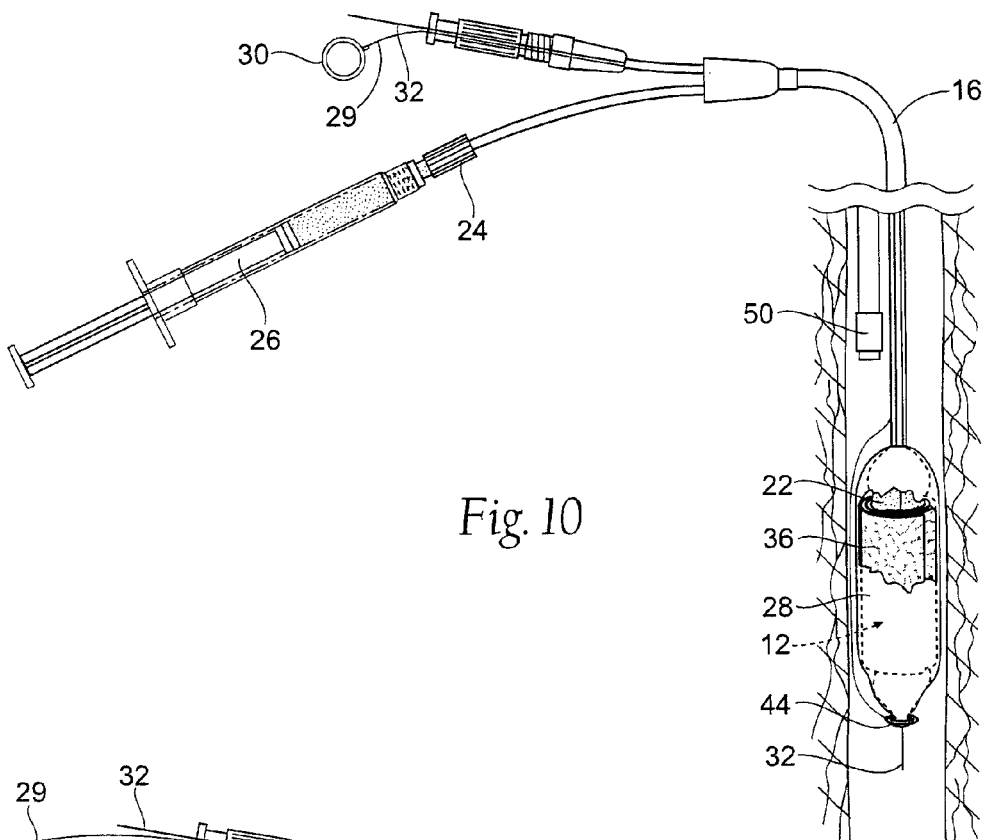
FIGS. 10 to 13 show the use of the delivery system shown in FIG. 1 for introducing and applying a bandage structure within a body lumen or hollow body organ.

As shown in FIG. 1, the delivery device 14 can be sized and configured to accommodate passage over a guide wire 32. In this way, the delivery device 14 can be introduced over the guide wire 32 under direct visualization from an endoscope 50, as FIG. 10 shows. In this arrangement, the guide wire 32 runs next to the endoscope 50 and therefore leaves the working channel of the endoscope 50 free. In an alternative arrangement (see FIG. 15), the delivery device 14 can be sized and configured to be back-loaded through the working channel 52 of an endoscope 50. The working channel 52 of the endoscope 50 thereby serves to guide the delivery device 14 while providing direct visualization.

A. The Tissue Bandage Structure

The size, shape, and configuration of the bandage structure 12 shown in FIG. 1 can vary according to its intended use, which includes taking into account the topology and morphology of the site to be treated and the age/status of the patient (e.g., adult or child). The tissue bandage structure 12 is desirably flexible and relatively thin so that it can be rolled or folded upon itself for deployment in a low profile condition, as FIGS. 2 to 5 show. The tissue bandage structure 12 can be rectilinear, elongated, square, round, oval, or a composite or complex combination thereof. The shape, size, and configuration of tissue bandage structure 12 can be specially formed and adapted to the topology and morphology of the site of application, by cutting, bending, or molding in advance of use.

The tissue bandage structure 12 desirably includes an active therapeutic surface 36 for contacting tissue. The active surface 36 desirably comprises a biocompatible material that reacts in the presence of blood, body fluid, or moisture to become a strong adhesive or glue. The material of the active surface 36 can, alone or in combination with adhesive features, possess other beneficial attributes, for example, anti-bacterial and/or anti-microbial and/or anti-viral characteristics, and/or characteristics that accelerate or otherwise enhance coagulation and the body's defensive reaction to injury.

In one embodiment, the material of the active surface 36 of the tissue bandage structure 12 comprises a hydrophilic polymer form, such as a polyacrylate, an alginate, chitosan, a hydrophilic polyamine, a chitosan derivative, polylysine, polyethylene imine, xanthan, carrageenan, quaternary ammonium polymer, chondroitin sulfate, a starch, a modified cellulosic polymer, a dextran, hyaluronan or combinations thereof. The starch may be of amylase, amylopectin and a combination of amylopectin and amylase.

In a preferred embodiment, the biocompatible material of the active surface 36 comprises a non-mammalian material, which is most preferably poly [β-(1→4)-2-amino-2-deoxy-D-glucopyranose, which is more commonly referred to as chitosan.

The chitosan material is preferred because of the special properties of the chitosan. The chitosan active surface 36 is capable of adhering to a site of tissue injury along a body lumen in the presence of blood, or body fluids, or moisture. The presence of the chitosan active surface 36 stanches, seals, and/or stabilizes the site of tissue injury, while establishing conditions conducive to the healing of the site.

The chitosan material that is incorporated into the active surface 36 can be produced in conventional ways. The structure or form producing steps for the chitosan material are typically carried out from a chitosan solution employing techniques such as freezing (to cause phase separation), non-solvent die extrusion (to produce a filament), electro-spinning (to produce a filament), phase inversion and precipitation with a non-solvent (as is typically used to produce dialysis and filter membranes) or solution coating onto a preformed sponge-like or woven product. The filament can be formed into a non-woven sponge-like mesh by non-woven spinning processes. Alternately, the filament may be produced into a felted weave by conventional spinning and weaving processes. Improved compliance and flexibility can be achieved by mechanical manipulation during or after manufacture, e.g., by controlled micro-fracturing by rolling, bending, twisting, rotating, vibrating, probing, compressing, extending, shaking and kneading; or controlled macro-texturing (by the formation of deep relief patterns) by thermal compression techniques. The tissue bandage structure 12 can also comprise a sheet of woven or non-woven mesh material enveloped between layers of the chitosan material.

The active surface 36 that includes chitosan material presents a robust, permeable, high specific surface area, positively charged surface. The positively charged surface creates a highly reactive surface for red blood cell and platelet interaction. Red blood cell membranes are negatively charged, and they are attracted to the chitosan material. The cellular membranes fuse to chitosan material upon contact. A clot can be formed very quickly, circumventing immediate need for clotting proteins that are normally required for hemostasis. For this reason, the chitosan material is effective for both normal as well as anti-coagulated individuals, and as well as persons having a coagulation disorder like hemophilia. The chitosan material also binds bacteria, endotoxins, and microbes, and can kill bacteria, microbes, and/or viral agents on contact.

B. The Delivery Device

As FIG. 1 shows, the delivery device 14 includes a multi-lumen catheter tube 16 having a proximal end 18 and a distal end 20. The distal end 20 carries an expandable structure 22, which in the illustrated embodiment takes the form of an inflatable balloon. Other non-inflatable, but nevertheless expandable or enlargeable structures, can be used. The proximal end carries an actuator 30 and a coupling 24 which are manipulated in synchrony during operation of the expandable structure 22, as will be described in greater detail later.

The catheter tube 16 can be formed of conventional polymeric materials and include an interior lumen (not shown) that accommodates passage of a guide wire 32. The lumen also passes through the center of the expandable structure 22 as well. This makes it possible to guide the intraluminal deployment of the expandable structure 22 to an injury site within a body lumen or hollow body organ targeted for treatment.

The catheter tube 16 includes another lumen that communicates with the interior of the balloon 22. The proximal end 18 of the catheter tube 16 includes a coupling 24 for coupling an inflation device 26, such as a syringe or the like (see FIG. 1), in communication with the interior of the expandable structure 22. Operation of the inflation device 26 conveys an appropriate inflation medium (e.g., saline) into the expandable structure 22 to cause it to expand.

The catheter tube also includes a movable sheath 28. The sheath 28 comprises a material that is flexible and impermeable to water. A push-pull wire 30 is coupled to the sheath 28, which extends through another lumen within the catheter tube 16 and is coupled to an actuator 30 on the proximal end 18 of the catheter tube 16. Pushing on the actuator 30 advances the sheath 28 distally over the expandable structure 22 (as shown in phantom lines in FIG. 1). Pulling on the actuator 30 withdraws the sheath 28 proximally and free of the expandable structure 22 (as shown in solid lines in FIG. 1).

In use, the tissue bandage structure 12 is sized and configured to be carried about the expandable structure 22 in a generally collapsed condition during introduction within the body lumen or hollow body organ (see FIG. 10). The tissue bandage structure is also sized and configured to be enlarged in response to expansion of the expandable structure 22 (see FIG. 12) for placement into contact with tissue in the body lumen or hollow body organ.

FIGS. 2 to 5 show a representative embodiment of a flexible chitosan bandage structure 12 that can be readily deployed using the delivery device 14 in the manner just described. The bandage structure 12 includes an inert, non-stick, water impermeable coating 34 on a side opposite to the active chitosan surface 36. In use, it is the active chitosan surface 36 that is placed into contact with tissue. The inert, non-stick, water impermeable coating 34 makes it possible to roll or fold the chitosan surface 34 about the expandable structure 22 for deployment without sticking or adhering to the expandable structure 22 or itself.

Prior to intraluminal introduction of the delivery device 14 (see FIGS. 6 and 7), the sheath 28 is withdrawn, and the chitosan bandage structure 12 is mounted about the expandable structure 22, with the active chitosan surface 36 facing outward. In the illustrated embodiment, this is accomplished by wrapping the chitosan bandage structure 12 around the expandable structure 22, with the non-stick coating 34 facing the expandable structure 22. This corresponds to the generally collapsed condition described above, which provides a low profile condition for intraluminal introduction of the chitosan bandage structure 12.

Figure 6:
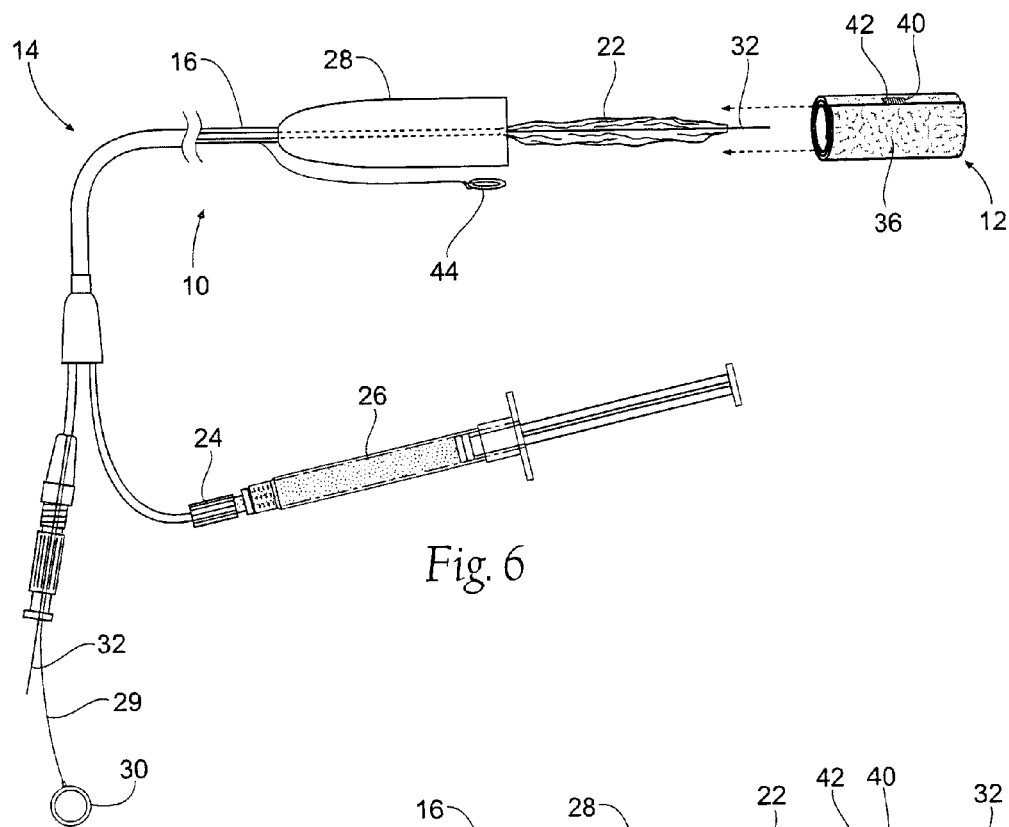
FIGS. 6 to 9 show the placement of a rolled bandage structure upon the expandable delivery structure that forms a part of the system shown in FIG. 1.
Figure 7:
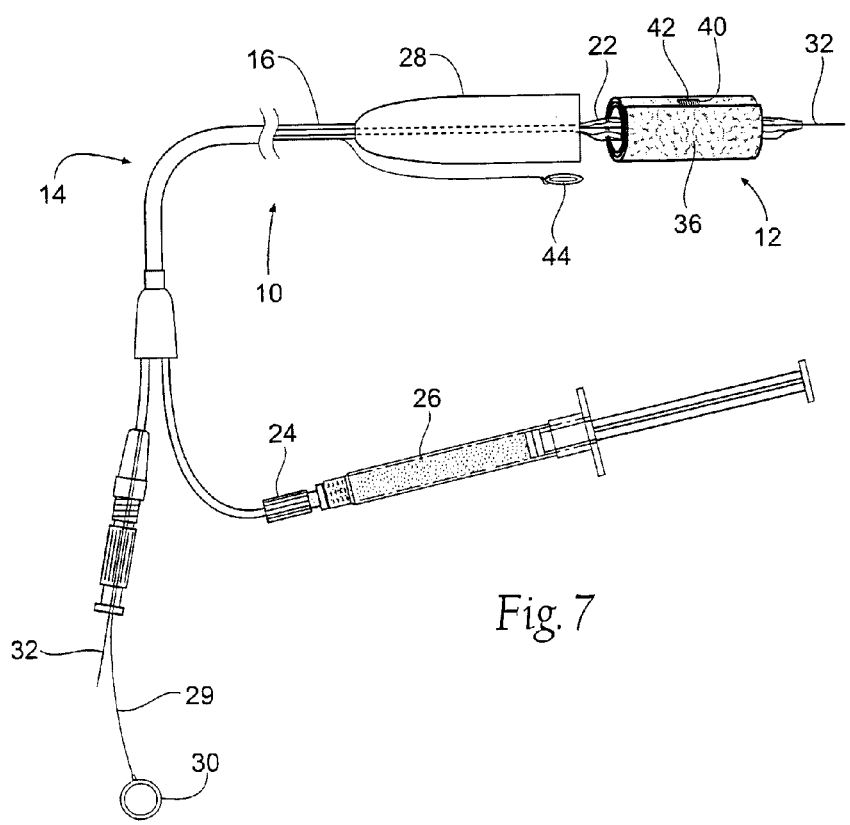
Figure 12:
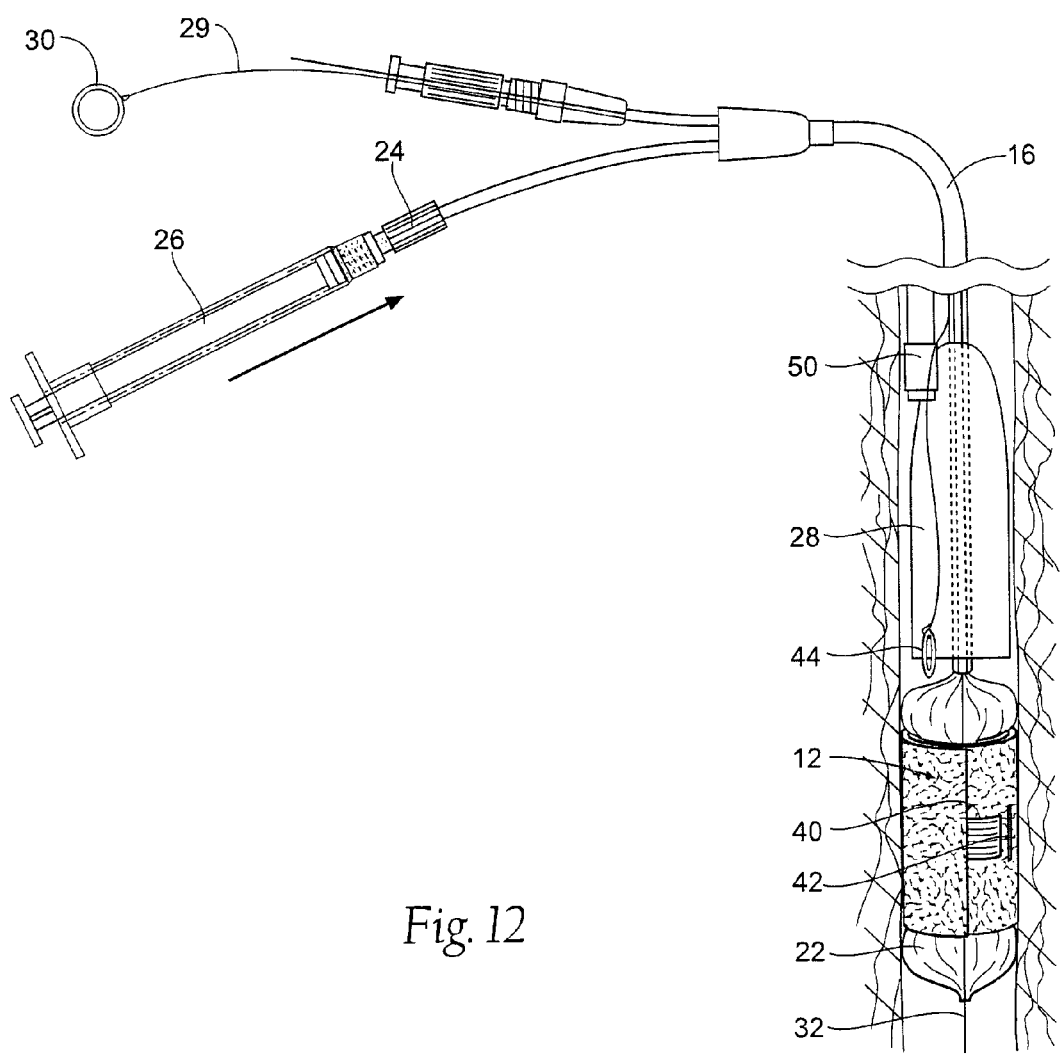

In this arrangement, the flexible bandage structure 12 (see FIGS. 2 to 5) has a rectangular shape with a tab 40 at one end. To secure the bandage in a rolled position about the expandable structure 22 (as shown in FIGS. 6 and 7), the tab can be inserted into a slit 42 formed in the chitosan bandage structure 12. The frictional force between the tab 40 and the walls of the slit 42 are sufficient to hold the bandage structure 12 in a rolled position. However, when pressure is applied from within the rolled bandage structure 12 (as is shown in FIG. 12 and will be described later), the tab 40 slides out of the slit 42 and the bandage structure 12 unfurls. Alternatively, the tab 40 and slit 42 can be replaced by a biodegradable tape with a perforation that will be more reliable in preventing premature deployment or unfurling of the bandage structure 12.

Figure 8:
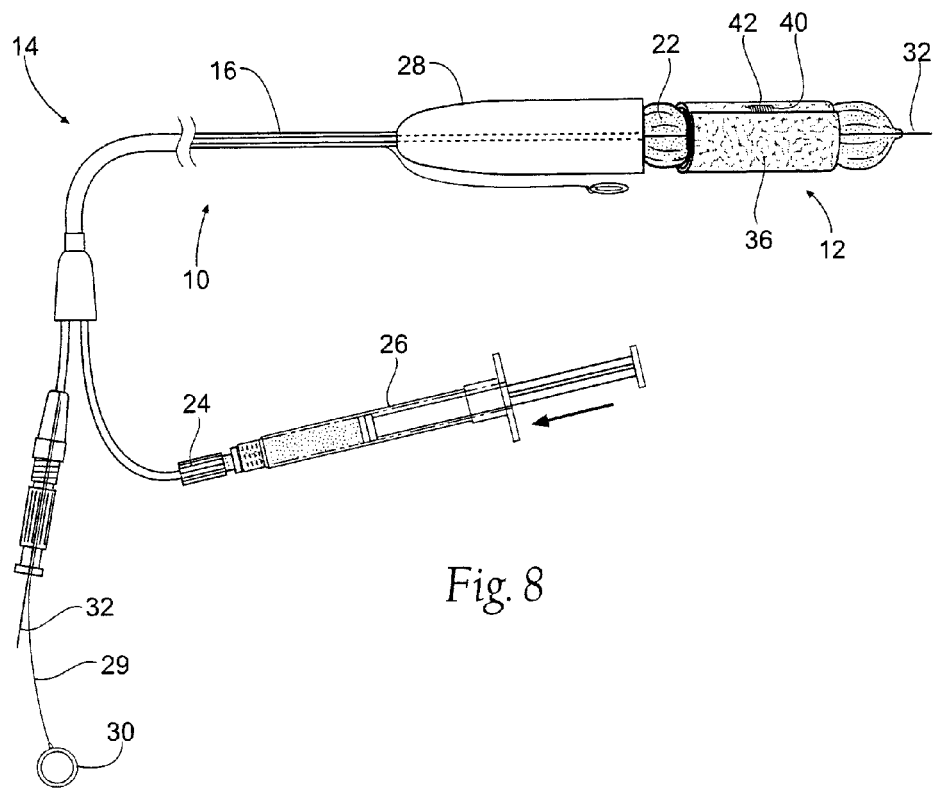
Figure 9:
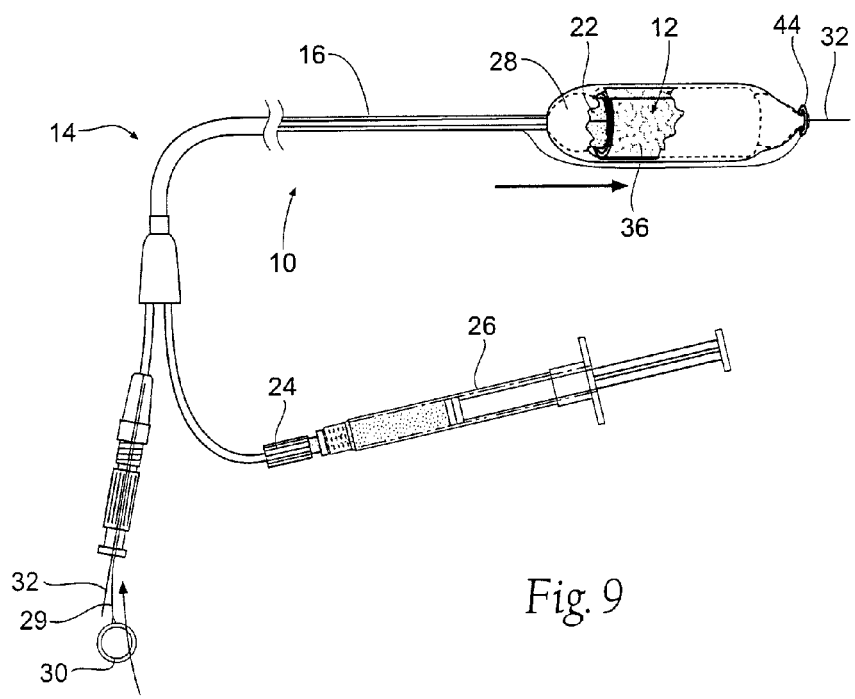

Prior to intraluminal introduction, the sheath 28 is advanced over the bandage structure 12 that has been wrapped about the expandable structure 22 (see FIGS. 8 and 9). As FIG. 9 shows, the distal end of the sheath 28 is closed by a frangible or otherwise releasable securing device 44. The securing device 28 holds the distal end of the sheath 28 closed.

The securing device 44 can be various constructed. It can, e.g., comprise a removable slip-knot that releases when the sheath is withdrawn, or a tearable perforated tab that tears when the sheath is withdrawn, or a ring that slides off or breaks when sheath is withdrawn.

In this position, the sheath 28 prevents contact between the active chitosan surface 36 and the mucosa during introduction until the instance of application. The sheath 28 protects the bandage structure 12 from becoming moist until the sheath 28 is moved proximally to reveal the bandage structure 12.

Prior to insertion into the body lumen (see FIG. 8), the expandable structure 22 is desirably partially enlarged by introduction of the inflating media (e.g., to about 0.25 atm) to create bulbous forms on each side of the bandage structure 12 as shown in FIG. 8. This partial expansion prevents the bandage structure 12 from migrating from the center of the expandable structure 22 during the introduction, but does not otherwise unfurl the bandage structure 12, which remains in the generally collapsed condition.

Figure 11:
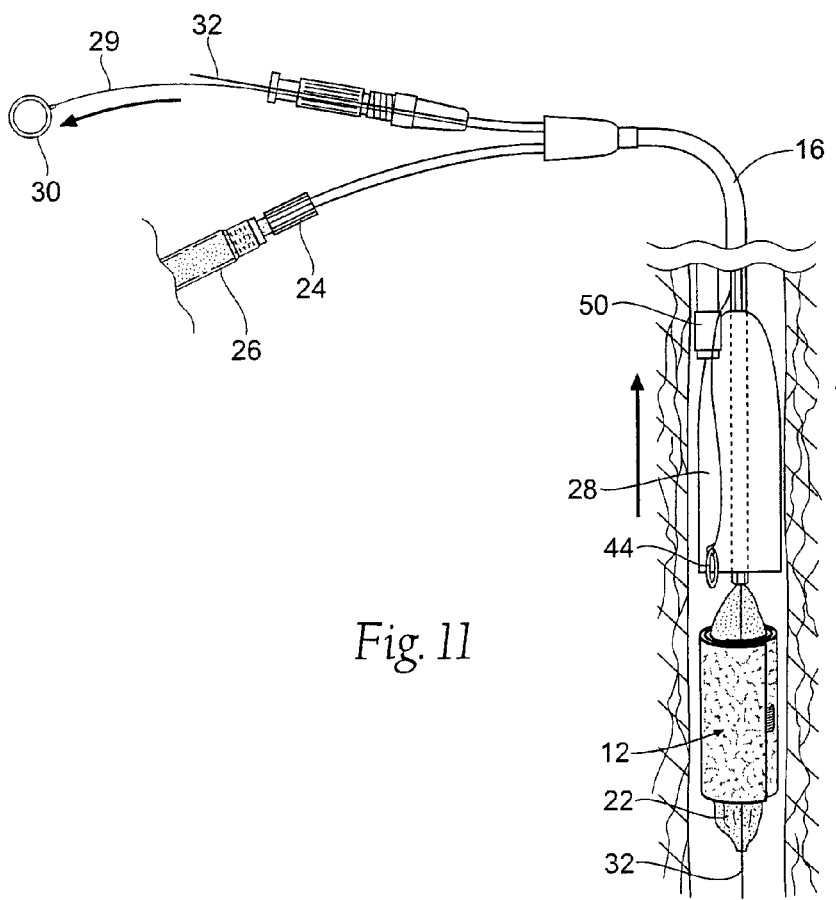

As will also be described later, when it is desired to deploy the bandage structure 12, the sheath 28 is withdrawn (see FIG. 11) and subsequent expansion of the expandable structure 22 (see FIG. 12) provides enough force to unfurl the bandage structure 12 into contact with an interior wall of the body lumen or hollow body organ.

II. Use of the Delivery System

The delivery system 10 makes possible the deployment of a chitosan bandage structure 12 within a body lumen or hollow body organ under endoscopic visualization, e.g., to treat an injury of the esophagus or other area of the gastrointestinal tract.

Figure 13:
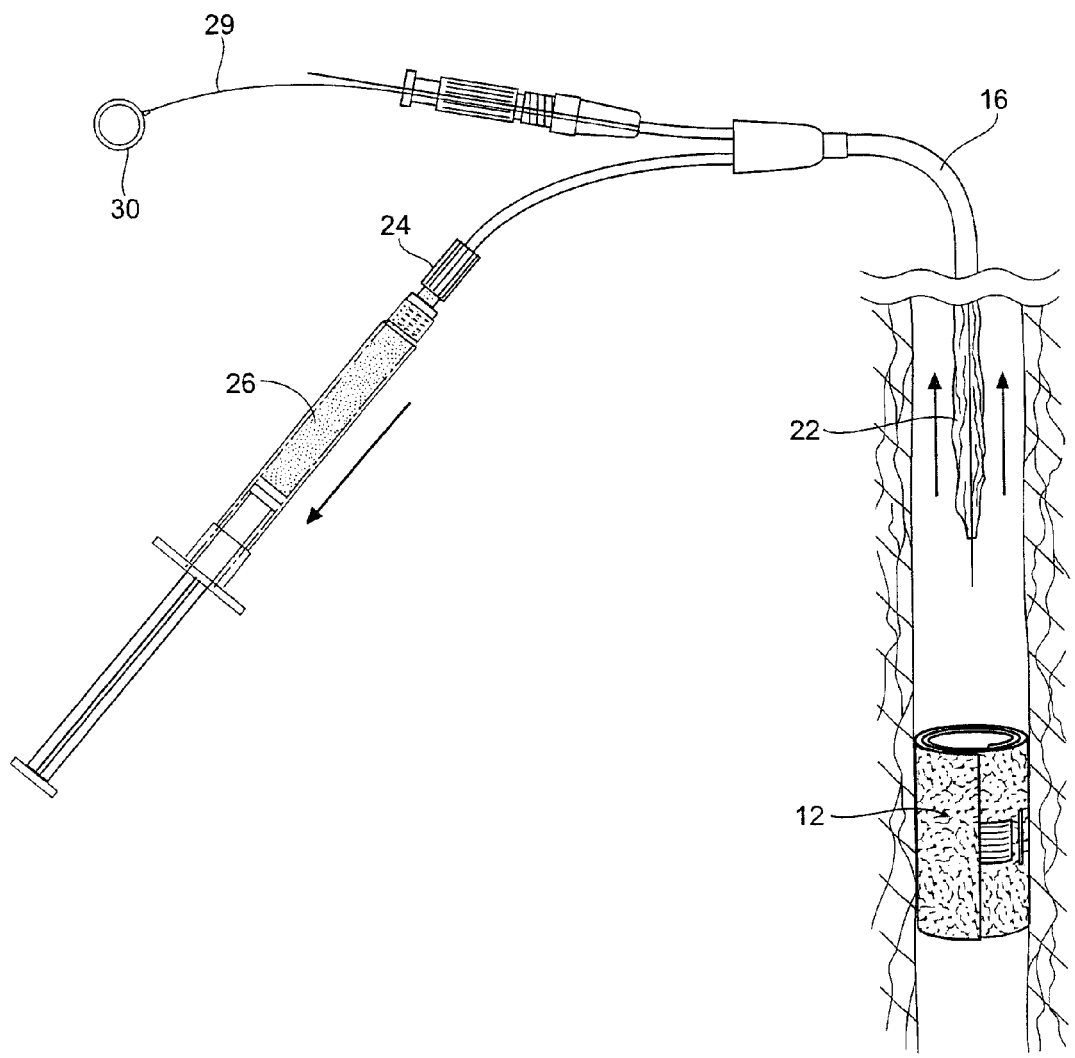
Figure 15:
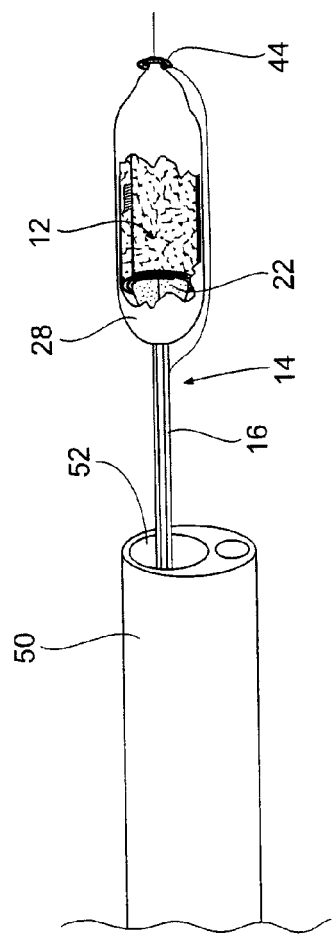
FIG. 15 shows the system shown in FIG. 1 back-loaded into the working channel of an endoscope.

As FIGS. 6 to 9 show, the chitosan bandage structure 12 can be wrapped and secured around the expandable structure 22 and enclosed during introduction with the removable sheath 28. The delivery device 12 can be deployed either over a guide wire 32 alongside an endoscope 50 (as FIG. 10 shows) or through the working channel of an endoscope (as FIG. 15 shows). Once the chitosan bandage structure 12 is positioned correctly over an injury site, the removable sheath 28 is pulled back (see FIG. 11) to uncover the chitosan bandage structure 12 for deployment. Subsequent expansion of the expandable structure 22 (see FIG. 12) expands and unfurls the chitosan bandage structure, holding it against the mucosa circumferentially at the site of injury. After an appropriate holding time (e.g., about three minutes), the expandable structure 22 is collapsed, and the delivery device 14 is withdrawn (see FIG. 13), leaving the chitosan bandage structure 12 at the injury site. During the entire procedure, the endoscope 50 provides direct visualization.

As the chitosan bandage structure 12 unfurls, it covers a circumferential section of the body lumen or hollow body organ and adheres to it. The properties of the active chitosan surface 36 serve to moderate bleeding, fluid seepage or weeping, or other forms of fluid loss, while also promoting healing. Due to the properties of the chitosan, the active surface 36 can also form an anti-bacterial and/or anti-microbial and/or anti-viral protective barrier at or surrounding the tissue treatment site within a body lumen or hollow body organ. The active surface 36 (whether or not it contains a chitosan material) can also provide a platform for the delivery of one or more therapeutic agents into the blood stream in a controlled release fashion. Examples of therapeutic agents that can be incorporated into the active surface 36 of the bandage structure 12 include, but are not limited to, drugs or medications, stem cells, antibodies, anti-microbials, anti-virals, collagens, genes, DNA, and other therapeutic agents; hemostatic agents like fibrin; growth factors; Bone Morphogenic Protein (BMP); and similar compounds.

The system 10 thereby makes possible an intraluminal delivery method that (i) locates and identifies the site of injury using an endoscope 50 and correlating video monitor; (ii) passes a guide wire 32 into the site of injury; (iii) positions the distal end of the delivery device 14 over the guide wire 32 (see FIG. 10) at the site of injury while viewing the area with the endoscope 50, which is positioned alongside the catheter tube 14; (iv) when positioned over the site of injury, as confirmed by the endoscope 50, pulls the actuator 30 on the proximal end of the catheter tube 14 (see FIG. 11) to withdraw the sheath 28 (also thereby breaking or otherwise releasing the security device 44) to unsheath and expose the chitosan bandage structure 12; (v) expands the expandable structure 22 (e.g., inflate the balloon) for a prescribed period (e.g., about three minutes) (see FIG. 12) to unfurl the bandage structure 12 and hold the active surface 36 of the bandage structure 12 against mucosa; (vi) after the prescribed holding period, collapses the expandable structure 22 (e.g. deflate the balloon) and removes the delivery device 12 and guide wire 32 (see FIG. 13), while continuing to monitor with the endoscope 50, if desired.

Figure 14:
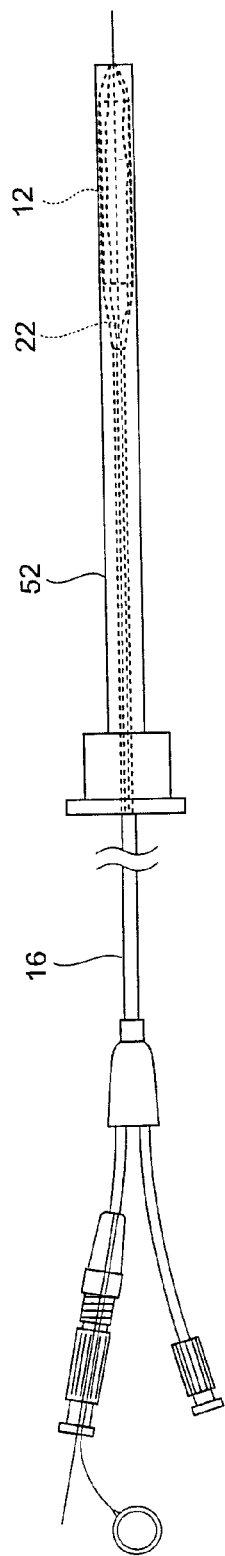
FIG. 14 shows an optional over-tube that can be used in association with the system shown in FIG. 1.

Various modifications of the above-described method can be made. For example (see FIG. 14), between (ii) and (iii), an over-tube 52 may be inserted in the body lumen to serve as a delivery sheath as well as a further water impermeable barrier between the device and the mucosa. As another example (see FIG. 15), the actuator 30 and coupling 24 can be separated from the proximal end of the catheter tube 14, and the catheter tube 14 back-loaded (proximal end first) through the working channel 52 of an endoscope 50. Once back-loaded, the proximal components are re-connected to the catheter tube 14. This arrangement uses the working channel 52 of the endoscope as a delivery sheath, instead of or in combination with a guide wire and/or an over-tube.

The shape, shape, and configuration of the expandable body and the bandage structure 12 can modified to accommodate varying anatomies encountered within a body lumen or hollow body organ, such as the gastrointestinal tract. This expands the possible use of the delivery system 10 greatly. For example, in esophagogastrectomies, an anastomosis between the stomach and the esophagus is created where an asymmetric expandable structure 22 and a bandage structure 12 can be deployed by the system 10 to cover the suture lines of the anastomosis. In addition, the size and shape of the expandable structure 22 can be altered to accommodate deployment of a bandage structure 12 in the duodenum or stomach.

The intraluminal delivery method as described utilizes the catheter-based delivery device 12, as described, to introduce a flexible, relatively thin chitosan bandage structure 12, as described, in an low profile condition and covered with a water impermeable layer to a targeted treatment site within a body lumen or hollow body organ, e.g. to treat esophageal injury. The delivery method prevents the active chitosan surface 36 of the bandage structure 12 from contacting the mucosa until the bandage structure 12 positioned in a desired position over the injury.

III. Conclusion

It has been demonstrated that a therapeutic bandage structure can be introduced and deployed within a body lumen or hollow body organ using an intraluminal delivery system 10 under endoscopic guidance.

It should be apparent that above-described embodiments of this invention are merely descriptive of its principles and are not to be limited. The scope of this invention instead shall be determined from the scope of the following claims, including their equivalents.

We claim:

1. A method for intraluminal delivery of a bandage structure within a body lumen or hollow body organ of the gastrointestinal tract or esophagus, comprising the steps of:
   providing a delivery system comprising:
      a rolled chitosan bandage having a tab and a slit formed therein, and wherein said chitosan bandage is releasably held in a rolled position by the tab inserted into the slit prior to positioning the bandage within the body lumen or the hollow body organ, has hemostatic properties, and an external active surface that reacts in the presence of a body fluid to become a strong adhesive;
      an expandable structure supporting said chitosan bandage wherein the tab is inserted into the slit; and
      a removable sheath enclosing said chitosan bandage;
   positioning the delivery system within said body lumen or hollow body organ so that the chitosan bandage is positioned over an injury site;
   removing the removable sheath when the chitosan bandage is positioned over the injury site;
   expanding the expandable structure to apply pressure from within the chitosan bandage so that the tab slides out of the slit and locates outside an outer surface of the bandage as the rolled chitosan bandage unfurls;
   adhering the chitosan bandage to said injury site; and
   removing the expandable structure.

2. The method according to claim 1, further including endoscopic visualization.

3. The method of claim 1, wherein the delivery system is deployed over a guide wire alongside an endoscope.

4. The method of claim 1, wherein the delivery system is deployed through a working channel of an endoscope.

5. The method of claim 1, wherein the rolled chitosan bandage includes a non-stick coating on a side opposite to the active surface.

6. The method of claim 1, further including holding the chitosan bandage against said injury site for a holding time of about three minutes.

7. The method of claim 1, further including closing the removable sheath using a releasable securing device.

8. The method of claim 1, wherein the body lumen or hollow body organ is an esophagus.

9. The method of claim 8, wherein the esophagus is hemorrhaging.

10. A method for intraluminal delivery of a bandage structure within a body lumen or hollow body organ of the gastrointestinal tract or esophagus, comprising the steps of:
    providing a delivery system comprising:
       a rolled chitosan bandage having a tab and a slit formed therein, wherein said chitosan bandage is releasably held in a rolled position by the tab inserted into the slit prior to positioning the bandage within the body lumen or the hollow body organ, has hemostatic properties, and an external active surface that reacts in the presence of a body fluid to become a strong adhesive; and
       an expandable structure supporting said chitosan bandage;
    protecting said chitosan bandage from moisture with a removable sheath;
    enlarging the expandable structure to create bulbous forms on each side of the chitosan bandage structure;
    positioning the delivery system within said body lumen or hollow body organ so that the chitosan bandage is positioned over an injury site;
    removing the removable sheath when the chitosan bandage is positioned over the injury site;
    expanding the expandable structure further so that the tab slides out of the slit and locates outside an outer surface of the bandage as the chitosan bandage unfurls and is held against and adheres to said injury site;
    covering a circumferential section of the body lumen or hollow body organ with the chitosan bandage;
    removing the expandable structure; and
    leaving the chitosan bandage at said injury site.

11. The method of claim 10, wherein the expandable structure is enlarged prior to positioning by the introduction of inflating media to 0.25 atm.

12. The method according to claim 10, further including endoscopic visualization.

13. The method of claim 10, wherein the delivery system is deployed over a guide wire alongside an endoscope.

14. The method of claim 10, wherein the delivery system is deployed through a working channel of an endoscope.

15. The method of claim 10, wherein the rolled chitosan bandage unfurls as the expandable structure applies pressure from within the bandage.

16. The method of claim 10, wherein the chitosan bandage includes a non-stick coating on a side opposite to the active surface.

* * * * *